US012775003B2

(12) United States Patent
Pamula

(10) Patent No.: US 12,775,003 B2
(45) Date of Patent: Oct. 27, 2026

(54) METHODS OF TRANSPORTING AND PROCESSING PHYSIOLOGICAL SAMPLES WITH A CENTRIFUGE-EQUIPPED UNMANNED AERIAL VEHICLE

(71) Applicant: Ganapathi Pamula, Cary, NC (US)

(72) Inventor: Ganapathi Pamula, Cary, NC (US)

( * ) Notice: Subject to any disclaimer, the term of this patent is extended or adjusted under 35 U.S.C. 154(b) by 0 days.

(21) Appl. No.: 18/643,407

(22) Filed: Apr. 23, 2024

(65) Prior Publication Data

US 2024/0310357 A1 Sep. 19, 2024

Related U.S. Application Data

(62) Division of application No. 17/114,161, filed on Dec. 7, 2020, now Pat. No. 11,965,874.
(Continued)

(51) Int. Cl.
*G01N 33/49* (2006.01)
*A61M 1/36* (2006.01)
(Continued)

(52) U.S. Cl.
CPC ......... *G01N 33/491* (2013.01); *A61M 1/3693* (2013.01); *B01D 21/262* (2013.01);
(Continued)

(58) Field of Classification Search
CPC .............. G01N 33/491; A61M 1/3693; A61M 2202/0415; A61M 2205/10;
(Continued)

(56) References Cited

U.S. PATENT DOCUMENTS

| | | | | |
|---|---|---|---|---|
| 10,052,641 | B2 * | 8/2018 | Letourneur | B04B 9/14 |
| 2016/0033966 | A1 * | 2/2016 | Farris | B64U 70/90 701/16 |

(Continued)

FOREIGN PATENT DOCUMENTS

| | | | |
|---|---|---|---|
| CN | 106882363 | A | 6/2017 |
| GB | 1108537 | A | 4/1968 |

(Continued)

OTHER PUBLICATIONS

Mayur Katariya, Dwayne Chung Kim Chung, Tristan Minifie, Harshit Gupta, Alifa Afiah Ahmad Zahidi, Oi Wah Liew, Tuck Wah Ng; Note: Biochemical samples centrifuged in-flight on drones. Rev. Sci. Instrum. Oct. 1, 2018; 89 (10): 106102. https://doi.org/10.1063/1.5031039.*

*Primary Examiner* — Claire X Wang
*Assistant Examiner* — Shuyi S. Liu
(74) *Attorney, Agent, or Firm* — E. Eric Mills; Nicholas P. Stadnyk; Maynard Nexsen PC

(57) ABSTRACT

A sample processing unit (SPU)-equipped drone for transporting and processing biological materials and method of using same is disclosed. In some embodiments, the presently disclosed SPU-equipped drone and method provide a drone equipped to carry an SPU and wherein the SPU may include a centrifuge arranged inside a temperature-controlled chamber and wherein the centrifuge may be used to process biological materials at the same time that the SPU-equipped drone is in flight. Further, a method of using the presently disclosed SPU-equipped drone for transporting and processing biological materials is provided.

10 Claims, 9 Drawing Sheets

Related U.S. Application Data

(60) Provisional application No. 62/944,416, filed on Dec. 6, 2019.

(51) Int. Cl.

| | |
|---|---|
| ***B01D 21/26*** | (2006.01) |
| ***B01L 3/00*** | (2006.01) |
| ***B04B 5/04*** | (2006.01) |
| ***B64C 39/02*** | (2023.01) |
| ***B64U 10/14*** | (2023.01) |
| ***B64U 30/29*** | (2023.01) |
| ***B64U 101/60*** | (2023.01) |

(52) U.S. Cl.

CPC .......... *B01L 3/5021* (2013.01); *B04B 5/0442* (2013.01); *B64C 39/024* (2013.01); *B64U 10/14* (2023.01); *B64U 30/29* (2023.01); *B64U 2101/60* (2023.01); *B64U 2201/20* (2023.01)

(58) Field of Classification Search

CPC .. A61M 2205/3368; A61M 2205/3576; A61M 1/0259; A61M 1/0281; B01D 21/262; B01L 3/5021; B01L 2200/185; B01L 2300/023; B01L 2400/0409; B04B 5/0442; B04B 5/0414; B04B 15/02; B64C 39/024; B64U 10/14; B64U 30/29; B64U 2101/60; B64U 2201/20; A01N 1/0236; A01N 1/0273

USPC ................ 494/10, 13, 14, 16, 20, 82, 84, 85

See application file for complete search history.

(56) References Cited

U.S. PATENT DOCUMENTS

| | | | | |
|---|---|---|---|---|
| 2018/0364157 | A1* | 12/2018 | Ghiraldi | A01C 21/007 |
| 2019/0015827 | A1 | 1/2019 | Berthier et al. | |
| 2019/0337607 | A1* | 11/2019 | Lee | B64C 11/48 |
| 2021/0061461 | A1 | 3/2021 | Williams | |

FOREIGN PATENT DOCUMENTS

| | | | | |
|---|---|---|---|---|
| JP | H06182259 | A | 7/1994 | |
| KR | 101644797 | B1 | 8/2016 | |
| WO | WO-2019059394 | A1 * | 3/2019 | G06Q 10/083 |
| WO | 2019206401 | A1 | 10/2019 | |
| WO | 2019212079 | A1 | 11/2019 | |

* cited by examiner

METHODS OF TRANSPORTING AND PROCESSING PHYSIOLOGICAL SAMPLES WITH A CENTRIFUGE-EQUIPPED UNMANNED AERIAL VEHICLE

CROSS-REFERENCE TO RELATED APPLICATIONS

The present application is a divisional application of U.S. patent application Ser. No. 17/114,161, entitled "Sample Processing Unit (SPU)-Equipped Drone for Transporting and Processing Biological Materials and Method of Using Same," filed Dec. 7, 2020, which claims priority to U.S. Provisional Patent App. No. 62/944,416, entitled "Sample Processing Unit on a Drone," filed on Dec. 6, 2019; the entire disclosures of which are incorporated herein by reference.

TECHNICAL FIELD

The presently disclosed subject matter relates generally to drones and/or autonomous unmanned aerial vehicles and more particularly to a sample processing unit (SPU)-equipped drone for transporting and processing biological materials and method of using same.

BACKGROUND

Drones are increasingly being utilized in the medical field. Currently, drones are being deployed to drop off medical supplies and some drones are starting to be considered for picking up medical supplies. For example, in emergency situations a drone may be utilized to transport human biological materials or samples to a facility for processing. In this scenario, the drone is used for transport only and, in particular, no processing of the biological sample occurs on the drone itself. The use of drones in emergency situations to transport biological samples (e.g., blood specimens, tissue, organs) may be beneficial to save lives. Therefore, to maximize this life saving benefit, new approaches are needed with respect to utilizing drones for drop-off, pick-up, and/or processing of biological materials.

SUMMARY

The invention provides sample processing unit (SPU)-equipped drone for transporting and processing biological materials and method of using same.

In some embodiments, the presently disclosed SPU-equipped drone may include an apparatus for transporting and processing biological materials. The drone may have a drone body and propellers. Legs may be optional. A sample processing unit (SPU) may be connected to the drone body. Further, a transmitter may operate the drone or the drone may operate autonomously.

In some embodiments, the transmitter may be a radio transmitter or smartphone or both.

In some embodiments, the SPU may include a thermally insulated container that is mechanically and thermally coupled to a temperature control device.

In some embodiments, the SPU-equipped drone may include control electronics for controlling the drone or the SPU or both the drone and the SPU. The control electronics may include a controller, a communications interface, and a global positioning system. In some embodiments, the controller may be an onboard computer or an application specific circuit board. In some embodiments, the communications interface may be any wired or wireless communication interface for connecting to a network. In some embodiments, the global positioning system may include a GPS receiver and an error correction component.

In some embodiments, the SPU the may include a centrifuge for processing one or more samples. The one or more samples may be a blood sample for plasma or serum separation. In some embodiments, the centrifuge may be gyro-stabilized.

In other embodiments, the centrifuge may include a motor with a shaft coupled to an arm arranged substantially horizontally, the arm may have a receptacle at each end of the arm, wherein each receptacle may hold a sample of the one or more samples, a dummy liquid or a weight, the sample, the dummy liquid, and the weight being substantially equal in weight. In some embodiments, the motor may be adapted to spin the arm to generate centrifugal forces to separate the components of the one or more samples.

In some embodiments, the SPU may include a thermally insulated container that is mechanically and thermally coupled to a temperature control device, and the centrifuge may be inside the thermally insulated container. In some embodiments, the temperature control device may have an arrangement of heat radiation fins. In other embodiments, the arrangement of heat radiation fins may be mounted on multiple sides of the thermally insulated container. In some embodiments, the thermally insulated container may be connected to the underside of the drone body, and the motor may be arranged at substantially the center of the drone body.

In other embodiments, the centrifuge may include two motors, each of the two motors with a motor shaft, coupled to two arms arranged substantially horizontally that has a receptacle at each end of the two arms for holding the one or more samples, the two motors coupled to two concentric sleeved shafts. In other embodiments, the one of the two motors may be geared to and drive the inner of the two concentric sleeved shafts, and the other of the two motors may be geared to and drive the outer of the two concentric sleeved shafts, and the two concentric sleeved shafts may be adapted to rotate in opposite directions.

In some embodiments, the centrifuge may include a motor with a motor shaft, two independent shafts, and a gear arrangement, wherein each of the two independent shafts may be coupled to an arm that has a receptacle at each of the arm, wherein the motor may be arranged substantially perpendicular to the two independent shafts, and wherein the gear arrangement may be adapted to rotate the two independent shafts in opposite directions.

The invention also provides a method. In some embodiments, the method may have the steps of: providing a sample processing unit (SPU)-equipped drone for transporting and processing biological materials, the SPU-equipped drone comprising: a drone having a drone body and propellers; and a sample processing unit (SPU) connected to the drone body; collecting a biological sample; placing the biological sample into the SPU-equipped drone; activating the SPU of the SPU-equipped drone for processing the biological sample at the same time of aerial transport. The method may further have the steps of: setting the receiving destination and deploying the SPU-equipped drone for aerial transport of the biological sample; notifying the destination of the incoming biological sample arriving by the SPU-equipped drone; executing a flight path of the SPU-equipped drone while at the same time processing the biological sample; receiving the SPU-equipped drone carrying the pre-processed biological sample at a destination; removing the pre-processed biological sample from the SPU-equipped drone; notifying the sender of the received pre-processed biological sample; and returning the SPU-equipped drone to sending destination or to another destination.

BRIEF DESCRIPTION OF DRAWINGS

Figure 1:
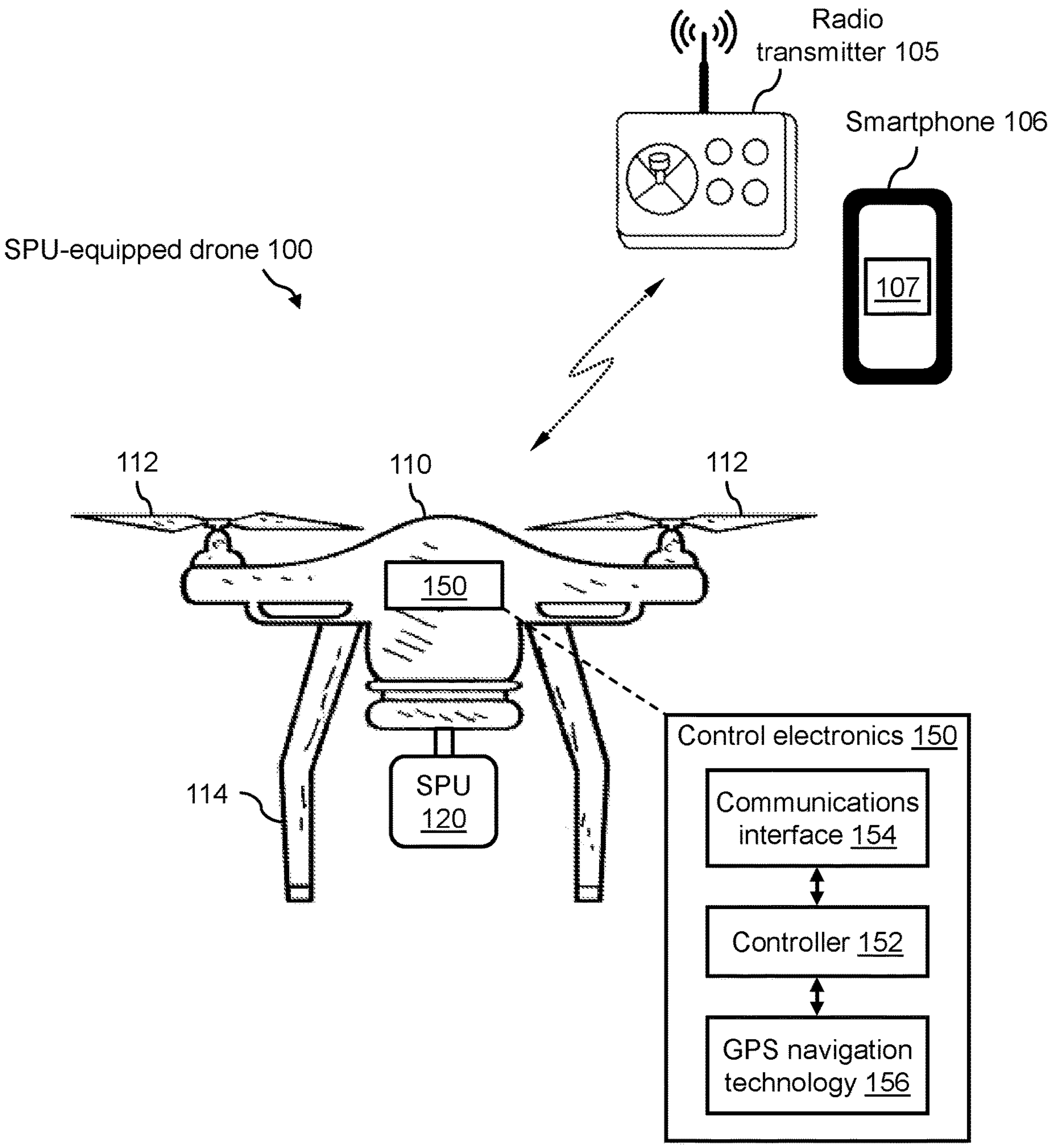
Figure 2:
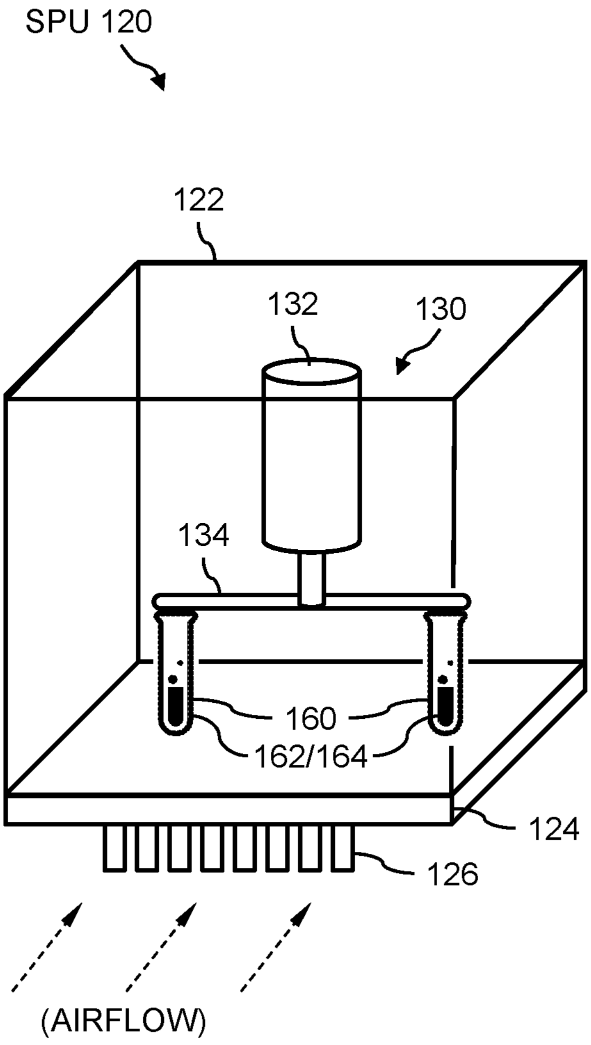
Figure 3:
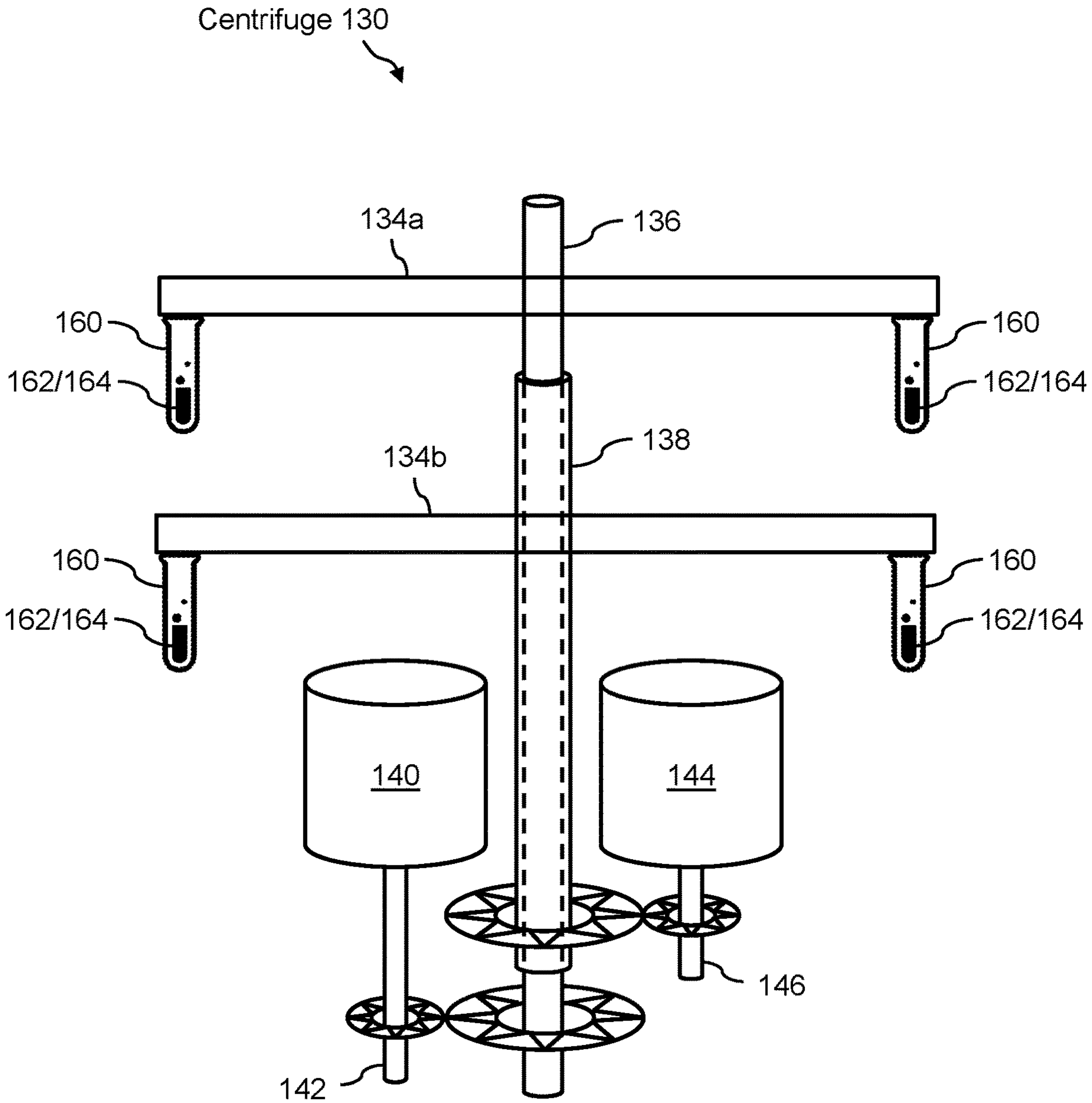
Figure 4:
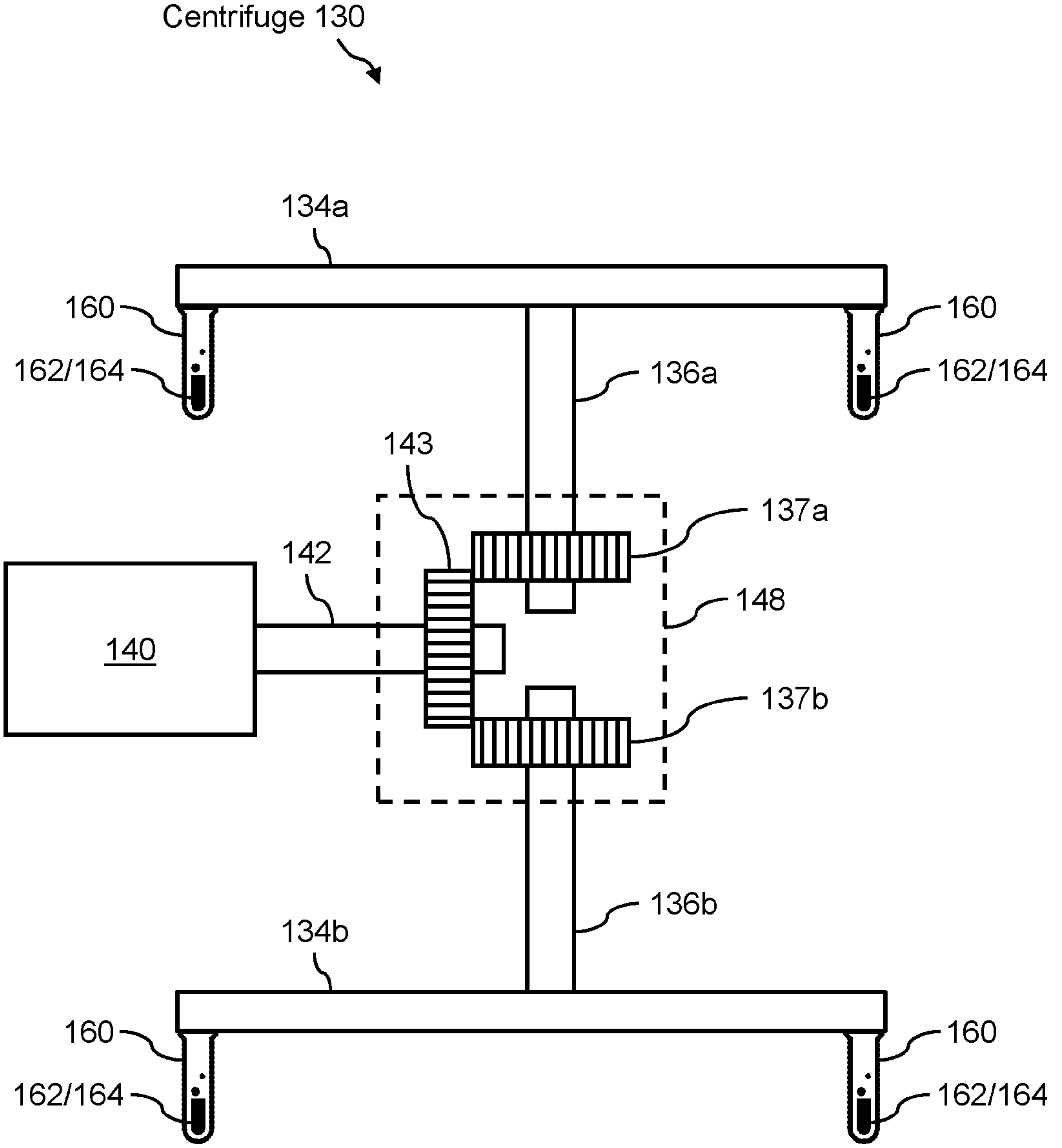
Figure 5:
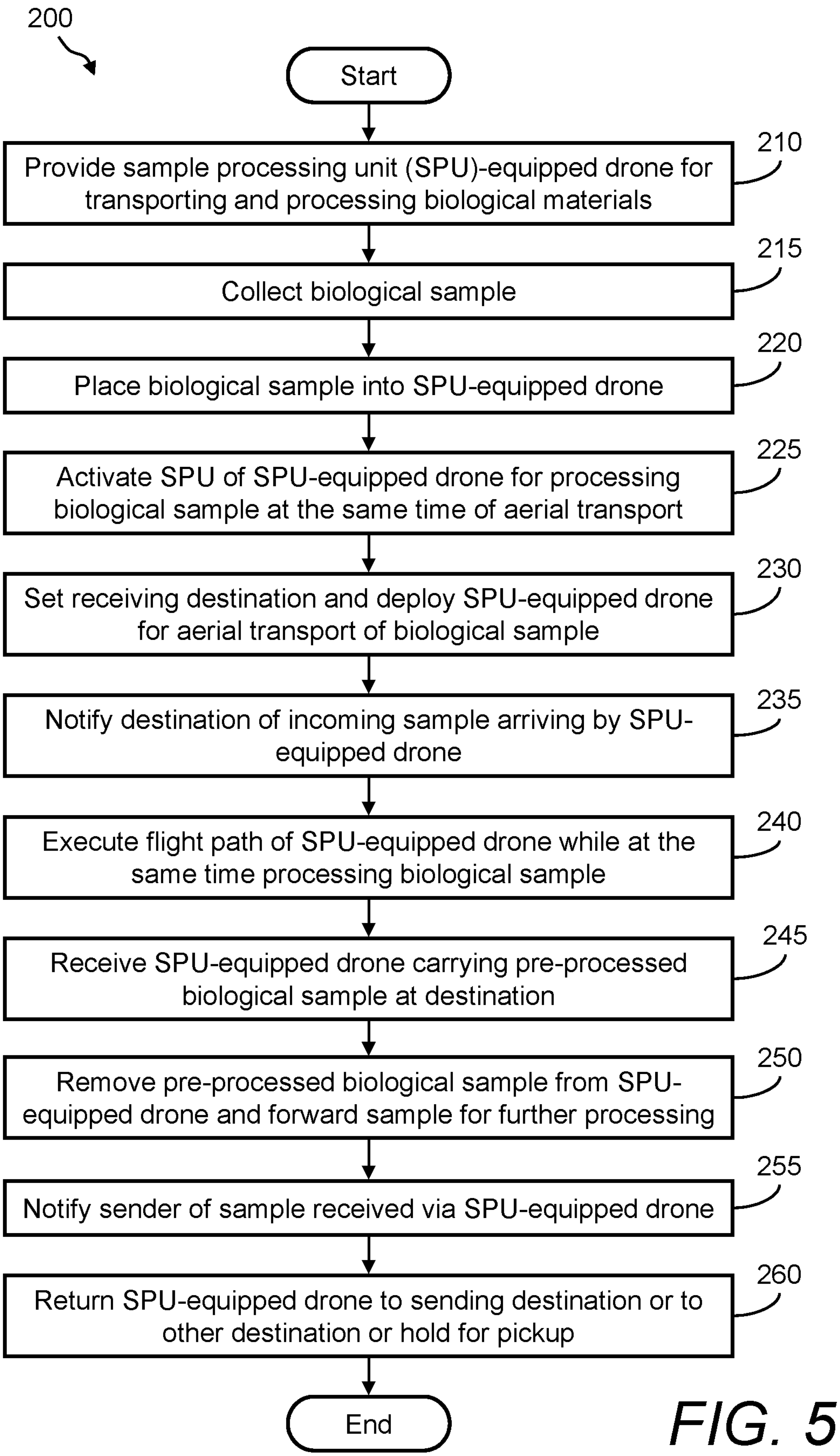
Figure 6:
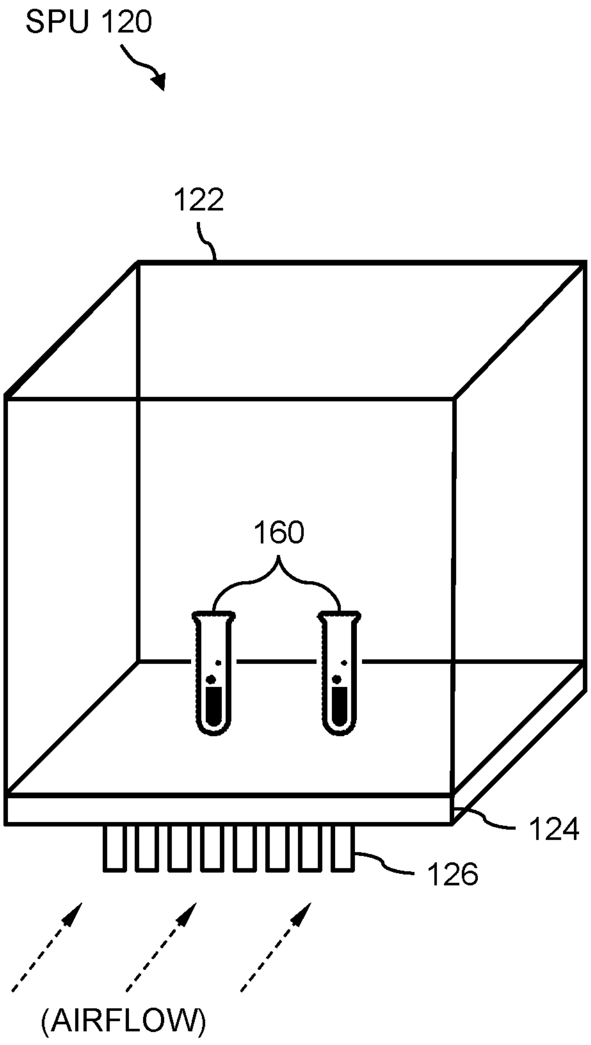
Figure 7:
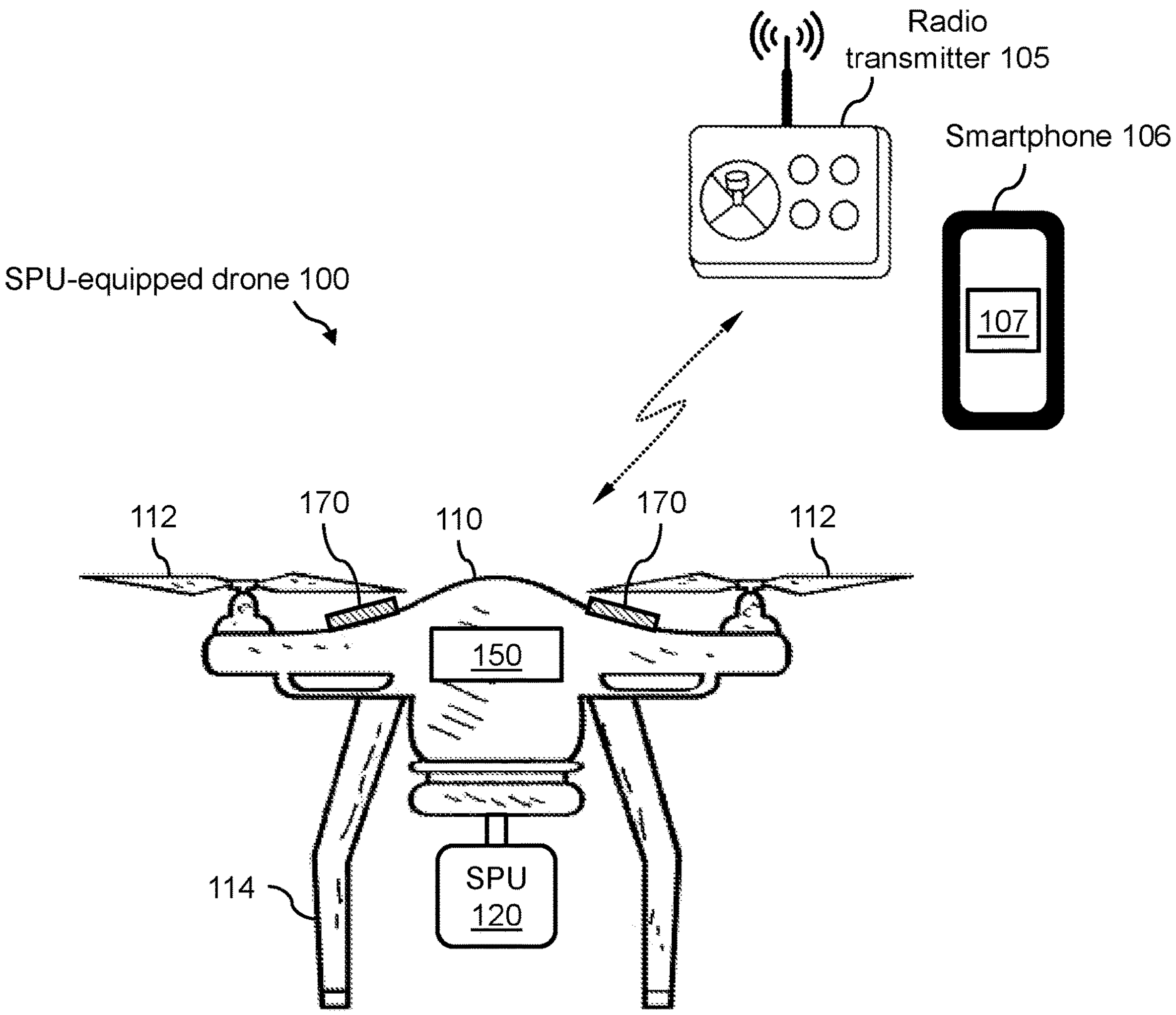
Figure 8:
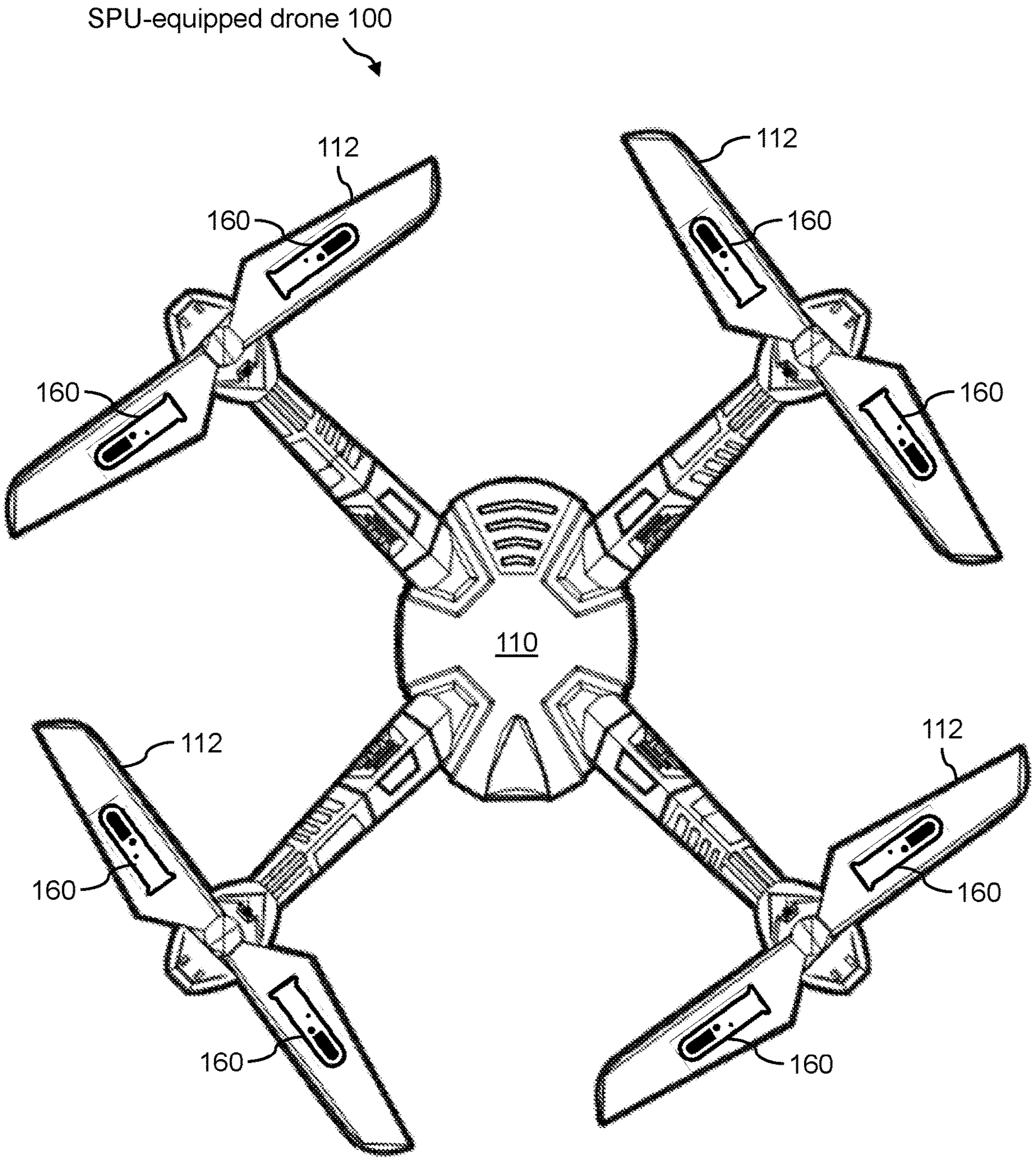
Figure 9:
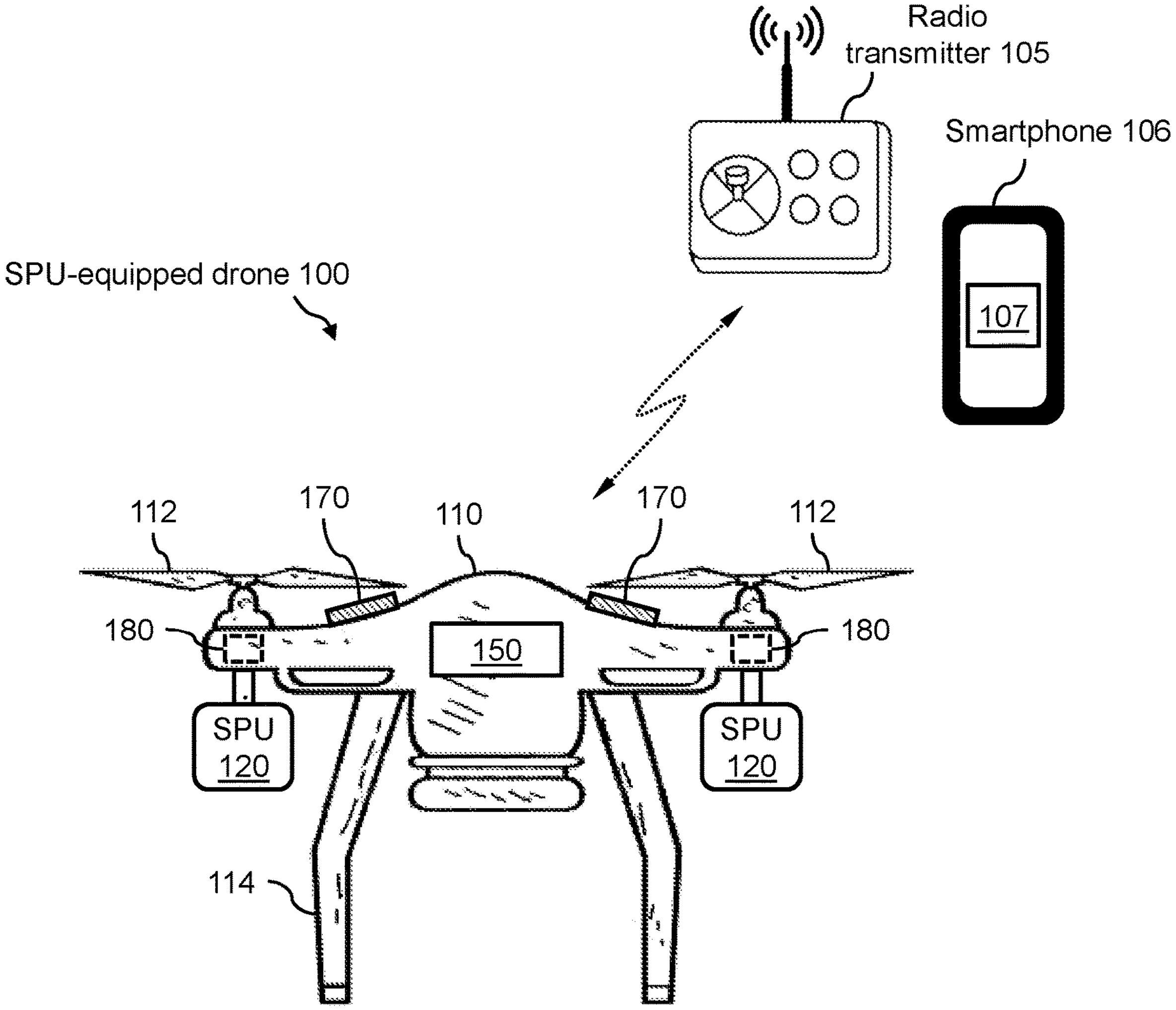

Having thus described the presently disclosed subject matter in general terms, reference will now be made to the accompanying drawings, which are not necessarily drawn to scale, and wherein:

FIG. 1 illustrates a side view of an example of the presently disclosed SPU-equipped drone for transporting and processing biological materials;

FIG. 2 illustrates a perspective view of an example of the SPU of the presently disclosed SPU-equipped drone and wherein the SPU includes a centrifuge;

FIG. 3 illustrates a schematic diagram of an example of a configuration of the centrifuge of the SPU that uses two motors to counter the centrifuge action;

FIG. 4 illustrates a schematic diagram of an example of a configuration of the centrifuge of the SPU that uses just one motor and a gear arrangement to spin two axles in opposite directions to counter the centrifuge action;

FIG. 5 illustrates a flow diagram of an example of a method of using the presently disclosed SPU-equipped drone for transporting and processing biological materials;

FIG. 6 illustrates a perspective view of another example of the SPU of the presently disclosed SPU-equipped drone and wherein the SPU includes temperature control;

FIG. 7 illustrates a side view of another example of the presently disclosed SPU-equipped drone for transporting and processing biological materials;

FIG. 8 illustrates a plan view of an example of the presently disclosed SPU-equipped drone that uses the drone propellers for centrifugation of the biological samples; and FIG. 9 illustrates a side view of an example of the presently disclosed SPU-equipped drone that uses the propeller motors for centrifugation of the biological samples.

DETAILED DESCRIPTION

The presently disclosed subject matter now will be described more fully hereinafter with reference to the accompanying drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a sample processing unit (SPU)-equipped drone for transporting and processing biological materials and method of using same.

In some embodiments, the presently disclosed SPU-equipped drone and method provide a drone equipped to carry an SPU and wherein the SPU may include a centrifuge arranged inside a temperature-controlled chamber and wherein the centrifuge may be used to process biological materials.

In some embodiments, the presently disclosed SPU-equipped drone and method provide a drone equipped to carry an SPU and wherein the SPU may be used to process biological materials, such as, but not limited to, blood, urine, saliva, nasal samples, bodily fluids, tissue, organs, and the like.

In some embodiments, the presently disclosed SPU-equipped drone and method provide a drone equipped to carry an SPU and wherein the SPU may be used to process a blood sample into plasma and/or serum.

In some embodiments, the presently disclosed SPU-equipped drone and method may be used to both transport and process biological materials at the same time. For example, the SPU of the presently disclosed SPU-equipped drone may be used to process biological materials at the same time that the SPU-equipped drone is in flight.

In some embodiments, the presently disclosed SPU-equipped drone and method provide in-flight processing of biological materials that may include, for example, centrifugation, separation, performance of analytical assays to quantitatively determine the components of sample, such as electrolytes, gases, proteins, metabolites, nucleic acids, cells, and other routinely-evaluated laboratory tests.

In some embodiments, the presently disclosed SPU-equipped drone and method provide a geo-enabled drone for transporting and processing biological materials.

Further, a method of using the presently disclosed SPU-equipped drone for transporting and processing biological materials is provided.

Referring now to FIG. 1 is a side view of an example of the presently disclosed SPU-equipped drone 100 for transporting and processing biological materials. SPU-equipped drone 100 may include, for example, a drone body 110, a standard configuration of propellers 112 (e.g., a configuration of four propellers 112), and a set of legs 114 (e.g., four legs 114). Legs 114 support SPU-equipped drone 100 when not in flight. Drone 110 is for illustrative purposes and can include any single-rotor drones, multi-rotor drones, helicopter drones, fixed-wing drones, fixed-wing hybrid drones, small drones, micro drones, tactical drones, medium drones, large drones, reconnaissance drones, delivery drones, alternative-powered drones, and other winged and rotor drones. Further, a transmitter such as radio transmitter 105 is provided for operating SPU-equipped drone 100 by radio control. The radio transmitter 105 may be, for example, a multi-channel radio transmitter with standard controls as well as any customized controls/interfaces for operating SPU-equipped drone 100. Additionally, in place of or in addition to radio transmitter 105, a smartphone 106 (or any smart device) that includes a mobile app 107 may be used to control and/or communicate with SPU-equipped drone 100.

SPU-equipped drone 100 also includes an SPU 120 that may be mechanically and electrically connected to the underside of drone body 110. SPU 120 may be sized to fit below drone body 110 and within the space defined by legs 114. The SPU 120 may be placed anywhere on the drone including, for example, above the drone or right below the propellers 112. Further, the weight of SPU 120 may be not to exceed the carrying capability of SPU-equipped drone 100. Further, the shape of SPU 120 may be suitably aerodynamic to not disturb the flight capabilities of SPU-equipped drone 100. More details of an example of SPU 120 and various features thereof are shown and described hereinbelow with respect to FIG. 2, FIG. 3, and FIG. 4.

While SPU-equipped drone 100 may include standard components (e.g., controller, propeller motors, sensors, onboard camera, batteries (not shown)) for flying, SPU-equipped drone 100 may also include other control electronics 150 with respect to controlling SPU 120 and using SPU-equipped drone 100 for transporting and processing biological materials. In one example, control electronics 150 may include a controller 152, a communications interface 154, and global positioning system (GPS) navigation technology 156. In another example, control electronics 150 may include gyroscope, accelerometer, barometer, magnetometer, LIDAR, radar, and other sensors.

Controller 152 of the control electronics 150 may be used to manage the overall operations of SPU-equipped drone 100 or at least those of SPU 120. Controller 152 may be any standard controller or microprocessor device that is capable of executing program instructions. In one example, controller 152 may be an onboard computer, such as a Raspberry Pi (i.e., Raspberry Pi 3 platform available from The Raspberry Pi Foundation (United Kingdom)), or an application specific circuit board. A certain amount of data storage (not shown) may be associated with controller 152.

Communications interface 154 of the control electronics 150 may be any wired and/or wireless communication interface for connecting to a network (not shown) and by which information may be exchanged with other devices connected to the network. In one example, communications interface 154 may be used to communicate wirelessly with radio transmitter 105 and/or smartphone 106 and/or any computer equipped with radio telemetry transceivers (not shown). Examples of wired communication interfaces may include, but are not limited to, USB ports, RS232 connectors, RJ45 connectors, Ethernet, and any combinations thereof. Examples of wireless communication interfaces may include, but are not limited to, an Intranet connection, Internet, ISM, Bluetooth® technology, Bluetooth® Low Energy (BLE) technology, Wi-Fi, Wi-Max, IEEE 402.11 technology, ZigBee technology, Z-Wave technology, 6LoWPAN technology (i.e., IPv6 over Low Power Wireless Area Network (6LoWPAN)), ANT or ANT+ (Advanced Network Tools) technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols.

GPS navigation technology 156 of the control electronics 150 may include any device that can determine its geographical location to a certain degree of accuracy. Accordingly, SPU-equipped drone 100 is a geo-enabled drone. For example, GPS navigation technology 156 may include a GPS receiver, such as a global navigation satellite system (GNSS) receiver. A GPS receiver may provide, for example, any standard format data stream, such as a National Marine Electronics Association (NMEA) data stream. GPS navigation technology 156 may also include an error correction component (not shown), which may be any mechanism for improving the accuracy of the geo-location data. In another embodiment, GPS navigation technology 156 may include any device or mechanism that may determine location by any other means, such as by performing triangulation (e.g., triangulation using cellular radiotelephone towers).

Referring now to FIG. 2 is a perspective view of an example of SPU 120 of the presently disclosed SPU-equipped drone 100 and wherein SPU 120 includes a centrifuge. In this example, SPU 120 may include a thermally insulated container 122 that is mechanically and thermally coupled to a temperature control device 124 that may have an arrangement of heat radiation fins 126. In one example, temperature control device 124 is arranged on the bottom of thermally insulated container 122. In one example, temperature control device 124 may be a thermoelectric cooling mechanism, such as a Peltier cooler/heater. Together, thermally insulated container 122 and temperature control device 124 provide a temperature-controlled chamber of SPU 120 that is suitable for processing biological materials.

In one example, a centrifuge 130 is arranged inside thermally insulated container 122 for processing one or more samples 162 that may be held, for example, in vials. A sample 162 may be any biological materials, such as, but not limited to, blood, urine, saliva, nasal samples, bodily fluids, tissue, and the like. In this example, centrifuge 130 may include a motor 132 whose shaft is coupled to an arm (or bar) 134 that has receptacles 160 (e.g., vials) for holding samples 162. Arm 134 may be arranged substantially horizontally and hold one receptacle 160 (one vial) on each end. Accordingly, in this example, motor 132 may be used to spin up to two samples 162 and/or dummy liquids or weights 164 held on arm 134.

In one example, thermally insulated container 122 and motor 132 may be connected to the frame or fuselage of SPU-equipped drone 100 with motor 132 facing down so that it does not interfere with the propeller rotors. For best stability, motor 132 of centrifuge 130 may be arranged at substantially the center of drone body 110 and with its axis of rotation substantially vertical. In one example, motor 132 may have about the same specifications as the propeller motors, though that may not be a requirement. In another example, centrifuge 130 may be gyro-stabilized when SPU-equipped drone 100 is not horizontal but has a pitch, yaw, or roll.

In one example, a sample tube (e.g., containing blood) may be loaded into each of the two receptacles 160. In another example, only one receptacle 160 is loaded with a sample tube (e.g., containing blood) and then to balance centrifuge 130 another equal weight (e.g., a dummy liquids or weights 164) may be placed in the other receptacle 160. Motor 132 of centrifuge 130 then spins arm 134 to generate centrifugal forces to separate the components of the sample 162 while SPU-equipped drone 100 is in flight or the process can commence even before SPU-equipped drone 100 takes off or after it lands. All the while, the one or more samples 162 are maintained at a certain temperature while being centrifuged. In one example, one or more blood samples 162 are maintained at a certain temperature while being centrifuged to prepare plasma or serum.

In SPU-equipped drone 100, thermal control may be achieved in multiple ways. For example, FIG. 2 shows thermally insulated container 122 with temperature control device 124 may be used cool the unit so that the samples are stable. Temperature control device 124 (i.e., the thermoelectric) may be programmed to setup and maintain at least 4° C. for the duration of flight and until the sample is delivered to its destination lab. The hot side of temperature control device 124 is placed outside of thermally insulated container 122 and heat radiation fins 126 are provided to efficiently and quickly dissipate the heat generated. The air flow during the flight of the drone is sufficient to dissipate the heat from heat radiation fins 126. SPU 120 of SPU-equipped drone 100 may also be set up to ensure that temperature control device 124 is turned on only when a certain air flow is detected so that the hot side does not get dangerously hot to impair the function by the addition of an air flow sensor. Further, heat radiation fins 126 may be mounted on multiple sides of thermally insulated container 122 and designed aerodynamically to reduce drag during flight while also dissipating heat. Heat can also be dissipated via a fan (not shown) that is driven by motor 132 or other motors on board or a passive fan that is driven by the motion of the drone itself. It can be noted that other forms of sample preservation to cool the samples may be utilized, such as ice packs, fans for convective cooling, using the ambient air flow, evaporative methods, advective cooling, radiative cooling, and other cooling methods.

Generally, serum or plasma separation is done by centrifuging the blood sample at about 1,000-2,000 xg for about 10 minutes and the presently disclosed SPU-equipped drone 100 may provide this capability. For example, to demonstrate how blood centrifugation may be performed in SPU 120 of SPU-equipped drone 100, certain blood centrifugation calculations are provided as follows:

Requirements:

(1) blood samples need to be spun at about 1,000-2,000 g to separate plasma or serum; and (2) time of separation is up to about 15 minutes.

Design:

(1) a typical drone motor has the following specifications: 935 KV and 5V; RPM (revolutions per minute) =KV*battery voltage=4,675 rpm;

(2) with a rotor that is 81.7 mm long: the relative centrifugal force generated is (g-force)=1.12*radius (mm)*(rpm/1,000)^2=2,000 xg; and (3) an alternative design may be to reduce the rotor length to 40 mm and increase the rpm to 6,682, with a different motor that has a higher KV rating, which still yields a 2,000 xg centrifugal force.

Further, to demonstrate that blood can be stored at 4° C. in SPU 120 of SPU-equipped drone 100, certain thermoelectric calculations are provided as follows:

Requirements:

(1) blood samples need to be stored at 4° C. after collection. Some physiological samples may need to be stored at −20° C.;

(2) storage time—from collection to delivery to the lab—approximately 30 minutes; and (3) Outside temperature maximum can be at 50° C.

Design:

(1) thermally insulated container 122—a box with polystyrene foam/Styrofoam insulator to keep the contents cool;

(2) temperature control device 124—a thermoelectric/Peltier with appropriate performance characteristics; and (3) calculations for an exemplary thermoelectric measuring 30 mm×30 mm×4.8 mm are made. To maintain a temperature differential of 46° C. (with an external temperature of 50° C.—desired temperature of 4° C.), an input current of 0.6 A at 6.5V is desired. Temperature is monitored with a temperature measurement device that maintains (proportional-integral-derivative) PID control of the thermoelectric based on the measured temperature. Typical lithium polymer (LiPo) batteries on a drone can provide the required voltage and current while still powering the drone flight.

In SPU 120 of SPU-equipped drone 100, the angular momentum generated by an extra motor (e.g., motor 132 of centrifuge 130) can be compensated to ensure stable flight. For example, counter-rotation to counter the centrifuge action may be provided by:

(1) adding an extra motor or motors to generate angular momentum in the opposite direction, as shown, for example, in FIG. 3;

(2) utilizing gears to spin another axle in the opposite direction, as shown, for example, in FIG. 4; and (3) generating extra yaw from the multicopter rotors on the drone itself.

Referring now to FIG. 3 is a schematic diagram of an example of a configuration of centrifuge 130 of SPU 120 that uses two motors to counter the centrifuge action. Generally, this configuration of centrifuge 130 provides a mechanism to generate counter angular momentum through use of two motors instead of just the one motor 132 shown in FIG. 2. Centrifuge 130 shown in FIG. 3 uses two concentric sleeved shafts rotating in opposite directions to counterbalance the angular rotation of the drone. For example, centrifuge 130 of FIG. 3 includes an inner shaft 136 connected to an arm **134*a* with its two receptacles 160. Centrifuge 130 of FIG. 3 also includes an outer shaft 138 connected to an arm 134*b* with its two receptacles 160. Inner shaft 136 is arranged concentrically with respect to outer shaft 138 with a sleeve through which inner shaft 136** may pass.

A motor 140 (the first motor) with its motor shaft 142 is geared to and drives inner shaft 136 with its arm **134*a*. A motor 144 (the second motor) with its motor shaft 146 is geared to and drives outer shaft 138 with its arm 134*b*. This configuration of two motors, will require no additional correction to the drone movement wherein this configuration utilizes two geared motors connected to shafts that will rotate them in different directions. Namely, motor 140 rotates inner shaft 136 and motor 144 drives outer shaft 138. Inner shaft 136 centrifuges one pair of receptacles 160 and outer shaft 138 centrifuges another pair of receptacles 160. Receptacles 160 can contain samples 162 or dummy liquids or weights 164** to keep the centrifuge balanced.

Referring now to FIG. 4 is a schematic diagram of an example of a configuration of centrifuge 130 of SPU 120 that uses one motor and a gear arrangement to spin two axles in opposite directions to counter the centrifuge action. For example, centrifuge 130 of FIG. 4 includes a shaft **136*a* connected at one end to an arm 134*a* with its two receptacles 160 and connected at the opposite end to a gear 137*a*. Centrifuge 130 of FIG. 4 also includes a shaft 136*b* connected at one end to an arm 134*b* with its two receptacles 160 and connected at the opposite end to a gear 137*b*. Centrifuge 130 of FIG. 4 also includes a motor 140 with a motor shaft 142 having a gear 143**.

In this example, shaft **136*a* and shaft 136*b* are arranged along the same line with gear 137*a* on shaft 136*a* facing gear 137*b* on shaft 136*b* and with arm 134*a* on shaft 136*a* facing away from arm 134*b* on shaft 136*b*. Motor 140 with motor shaft 142 is arranged substantially perpendicular to shaft 136*a* and shaft 136*b* and with gear 143 facing and engaging with gear 137*a* and gear 137*b* in a gear arrangement 148**.

In centrifuge 130 of FIG. 4, the one motor 140 is used to rotate two independent shafts (shafts **136*a*, 136*b*) in opposite directions using the gear arrangement 148 shown in FIG. 4. Gear 143 of motor 140 is arranged vertically and gears 137*a*, 137*b* on the shafts that hold the receptacles 160 are arranged horizontally. Due to the uncompensated torque of the single motor 140, SPU-equipped drone 100 may be subject to roll which can be compensated with its propeller motors correcting for the extra roll. By contrast, in centrifuge 130 of FIG. 3 that has two motors (e.g., motor 140, 144), the torque from spinning arm 134*a* cancels out the torque from spinning arm 134*b*. In centrifuge 130 of FIG. 4, gear arrangement 148 is designed to hold the axles, gears, and shafts in place. Again, to maintain balance, receptacles hold samples 162 or dummy liquids or weights 164. This arrangement is only exemplary as many other embodiments can be described. As another example, motor 140 can be placed vertically and another set of gears perpendicular to gears 137***a* and 137*b* can then drive arms 134*a* and 134*b* horizontally so that shafts 136*a* and 136*b* have the same axis of rotation as shaft 142 and not perpendicular as shown in FIG. 4. In this arrangement, extra roll may not be generated and any angular rotation can be compensated by a counter yaw.

Further, in SPU-equipped drone 100, the angular momentum generated by the centrifuge can also be compensated without any motors (e.g., as shown in FIG. 3 and FIG. 4) through extra yaw, roll, or pitch generated by the drone with the motors driving the propellers 112. The sensors (gyroscope and accelerometer) on the drone detect any extra yaw, roll, or pitch generated once the centrifuge is turned on and the computer on board the drone can utilize these values to provide counter yaw, counter, roll, or counter pitch to compensate and ensure the drone has a stable flight. Typically, a drone has a multitude of other sensors to help avoid any collisions for autonomous flight and maintain a flight path.

In some embodiments, multicopter motors of SPU-equipped drone 100 may be geared into SPU 120 to drive centrifuge 130 and spin samples 162. While an extra motor would allow centrifugation independent of the speed of the propellers, the motors driving the propellers can also be utilized to run the centrifuge with belts and gear mechanisms (similar to driving the rotor and the tail motor with the same motor in helicopter toys). The multicopter motors that are utilized for providing flight to the drone can also be used through the use of gears and a belt to transfer the rotary motion to spin samples 162 and provide necessary centrifugal forces for separation of its components.

Referring now to FIG. 5 is a flow diagram of an example of a method 200 of using the presently disclosed SPU-equipped drone 100 for transporting and processing biological materials. Method 200 may include, but is not limited to, the following steps.

At a step 210, an SPU-equipped drone for transporting and processing biological materials is provided. For example, the presently disclosed SPU-equipped drone 100 as described hereinabove with reference to FIG. 1 through FIG. 4 is provided for transporting and processing biological materials, such as samples 162 (e.g., blood, urine, saliva, nasal samples, bodily fluids, tissue, and the like).

At a step 215, a biological sample is collected. For example, a healthcare provider, such as an emergency medical technician (EMT) responding to a call, collects a sample 162 (e.g., blood, urine, saliva, nasal samples, bodily fluids, tissue, and the like) from a subject.

At a step 220, the biological sample is placed into the SPU-equipped drone. For example, the healthcare provider, such as the EMT, places a sample 162 into at least one receptacle 160 of SPU 120 of the presently disclosed SPU-equipped drone 100.

At a step 225, the SPU of the SPU-equipped drone is activated for processing biological sample at the same time of aerial transport. For example, the healthcare provider, such as the EMT, uses radio transmitter 105 and/or smartphone 106 to activate SPU 120 of the presently disclosed SPU-equipped drone 100. In this way, sample 162 may be processed at the same time that SPU-equipped drone 100 is in flight.

At a step 230, the receiving destination is set and the SPU-equipped drone is deployed for aerial transport of the biological sample. For example, the healthcare provider, such as the EMT, uses radio transmitter 105 and/or mobile app 107 on smartphone 106 to program the location (e.g., street address, GPS coordinates) of the receiving destination into the presently disclosed SPU-equipped drone 100. Then, the healthcare provider, such as the EMT, uses radio transmitter 105 and/or mobile app 107 on smartphone 106 to initiate or launch SPU-equipped drone 100, which is carrying the sample 162, into flight.

At a step 235, the target destination is notified of the incoming sample arriving by SPU-equipped drone. For example, the healthcare provider, such as the EMT, uses mobile app 107 on smartphone 106 (or any other communication means) to notify the target destination (e.g., hospital, lab, clinic) that one or more samples 162 are soon to be or are already in transit by the presently disclosed SPU-equipped drone 100. An estimated time of arrival may be given to the receiving party.

At a step 240, the flight path of the SPU-equipped drone is executed while at the same time the biological sample is processed. In one example, the flight path of the presently disclosed SPU-equipped drone 100 is executed automatically based on the target location information programed in method step 230. In another example, the flight path of the presently disclosed SPU-equipped drone 100 is guided manually by the sender or the receiver using an onboard camera.

Further, in this step, at the same time that the flight path is executing, the one or more samples 162 in SPU 120 are being processed. That is, during flight, the one or more samples 162 may be held at a desired temperature using temperature control device 124 of SPU 120 and centrifuged using centrifuge 130 of SPU 120. In one example, during flight, a blood sample 162 is processed to produce plasma and/or serum by the time that SPU-equipped drone 100 arrives at its destination. In-flight processing may include centrifugation, separation, performance of analytical assays to quantitatively determine the components of sample, such as electrolytes, gases, proteins, metabolites, nucleic acids, cells, and other routinely-evaluated laboratory tests.

At a step 245, the SPU-equipped drone carrying the pre-processed biological sample is received at the target destination. For example, the presently disclosed SPU-equipped drone 100 carrying the pre-processed biological sample 162 is received at the target destination (e.g., hospital, lab, clinic). For example, in the case of starting with a blood sample 162, the pre-processed biological sample 162 that is received at the target destination may be plasma and/or serum. Further, in this step, SPU-equipped drone 100 may be manually guided to a safe landing by the sender navigating via a drone onboard camera or just programmed to land autonomously using the onboard sensors (e.g., gyroscope, GPS, LIDAR).

At a step 250, the pre-processed biological sample is removed from the SPU-equipped drone and the sample is forwarded on for further processing if required. For example, a person at the destination (e.g., hospital, lab, clinic), removes the pre-processed biological sample 162 from SPU 120 of the presently disclosed SPU-equipped drone 100. Then, the receiving party forwards the pre-processed biological sample 162 on for further processing, if required. In the example of starting with a blood sample 162, the pre-processed biological sample 162 is plasma and/or serum. In the example of a nasal sample, prepared nucleic acids for infectious diseases may be extracted within the SPU 120 using centrifuge 130 or other chemical or mechanical methods and these prepared nucleic acids may be delivered for further processing. In yet another example, the prepared nucleic acids may be tested for certain sequences to identify pathogens and all processing complete by the time of arrival at the lab.

At a step 255, the sender is notified of sample being received via SPU-equipped drone. For example, the receiving party notifies the sending healthcare provider, such as the EMT, that the sample 162 has been received via the presently disclosed SPU-equipped drone 100. This notification may occur using any communications means. In one example, the sending healthcare provider, such as the EMT, receives notification via the mobile app 107 on smartphone 106. In this example, the receiving party may also have the mobile app 107 on a smartphone 106.

At a step 260, the SPU-equipped drone is returned to the sending destination or to any other destination or held for pickup. For example, the presently disclosed SPU-equipped drone 100 is returned (by flight) to the sending destination (which may be automatically stored when deployed) or to any other destination or held for pickup.

EXAMPLE

By way of example, the presently disclosed SPU-equipped drone 100 and method 200 may be used by an EMT responding to an emergency call. In this example, SPU-equipped drone 100 accompanies the ambulance (step 210). Once on site, the EMT draws blood or any physiological sample from the patient (step 215) and places it within SPU 120 of SPU-equipped drone 100 (steps 220, 225). The EMT then deploys SPU-equipped drone 100 (steps 230, 235). Deploying SPU-equipped drone 100 into flight will expedite the delivery of the sample to the laboratory for testing to start sooner while the patient is transported by an ambulance (steps 240, 245, 250). Accordingly, the test results may be available upon patient's arrival to the destination. Then, SPU-equipped drone 100 returns to the ambulance to serve on the next run (steps 255, 260). In non-emergency situations, the SPU-equipped drone 100 may be sent from a retail clinic or pharmacy or a hospital to a patient for retrieval of self-collected samples (such as capillary blood samples, urine, saliva, nasal samples, tears, sputum, feces, etc.) wherein SPU-equipped drone 100 is used to prepare the samples during flight while also maintaining the required temperature.

Referring now to FIG. 6 is a perspective view of another example of SPU 120 of the presently disclosed SPU-equipped drone 100. In this example, SPU 120 includes temperature control only and no centrifuging. That is, SPU 120 includes thermally insulated container 122 with temperature control device 124 but is absent centrifuge 130. Samples, such as nasal swabs, nasopharyngeal samples, mid turbinate samples, saliva, oropharyngeal samples, sputum, any respiratory specimens, urine, feces, and other physiological samples, can be transported without needing any centrifugation. Local healthcare facilities, such as hospitals, retail clinics, and laboratories, can send SPU-equipped drone 100 to pick up such samples, while preserving these samples at the prescribed temperature for fidelity in test results.

Referring now to FIG. 7 is a side view of another example of the presently disclosed SPU-equipped drone 100 for transporting and processing biological materials. SPU-equipped drone 100 is not limited to, for example, battery power only. In this example, SPU-equipped drone 100 may include additional energy sources, such as, but not limited to, solar panels 170 or other alternative sources of energy.

Referring now to FIG. 8 is a plan view of an example of the presently disclosed SPU-equipped drone 100 that uses the drone propellers for centrifugation of the biological samples. For example, the propellers 112 may include slots or compartments (not shown) for receiving and holding samples 162. In one example, two opposing propellers 112 include these slots or compartments while the remaining two propellers 112 do not. In another example, all four propellers 112 include these slots or compartments.

Referring still to SPU-equipped drone 100 shown in FIG. 8, a 3,750 rpm with a propeller length of 5 inches (or 127 mm) is sufficient to generate 2000 xg RCF, which is sufficient to separate components of blood. In a recent article (Rev. Sci. Instrum. 89, 106102 (2018); https://doi.org/10.1063/1.5031039), a similar idea was described with capillary tubes placed in the propellers of a drone motor. However, the propellers 112 of SPU-equipped drone 100 may be designed to handle larger sample collection tubes and not just capillary tubes. Additionally, the propellers 112 of SPU-equipped drone 100 may be shaped in such a way as to avoid flex that will be caused due to the centrifugal and lift forces generated. In another article (Anal. Chem. 2016, 88, 9, 4651-4660; https://doi.org/10.1021/acs.analchem.5b04153), a 3D printed attachment replaced the drone propellers so that centrifugation could be performed with the drone motors while the drone is on the ground and not in flight. The rotors driving the propellers 112 can also be used directly to spin an arm 134 that has a pair of samples 160 that are suspended below the propellers 112 and directly driven by the propeller motor, as shown for example in FIG. 9. Namely, FIG. 9 shows a side view of an example of the presently disclosed SPU-equipped drone 100 that uses propeller motors 180 for centrifugation of the biological samples in an SPU 120 located below each propeller 112.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments ±100%, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Although the foregoing subject matter has been described in some detail by way of illustration and example for purposes of clarity of understanding, it will be understood by those skilled in the art that certain changes and modifications can be practiced within the scope of the appended claims.

That which is claimed is:

1. A method for transporting and processing biological materials, comprising the steps of:

providing a sample processing unit (SPU)-equipped drone for transporting and processing biological materials, the SPU-equipped drone comprising: a drone having a drone body and propellers; and a sample processing unit (SPU) connected to the drone body, wherein the SPU comprises a centrifuge for processing a biological sample, the centrifuge including a mechanism to counter a force produced by a centrifuge action, the mechanism configured to generate a counterforce and comprising two motors coupled to two concentric sleeved shafts rotatable in opposite directions, the mechanism configured to operate independently of the propellers;

collecting the biological sample;

placing the biological sample into the SPU-equipped drone;

activating the SPU of the SPU-equipped drone at a sending destination; and processing the biological sample by at least the centrifuge at the same time of aerial transport.

2. The method of claim 1, further comprising the steps of:

setting a receiving destination and deploying the SPU-equipped drone for aerial transport of the biological sample;

notifying the receiving destination of the incoming biological sample arriving by the SPU-equipped drone;

executing a flight path of the SPU-equipped drone while at the same time processing the biological sample;

receiving the SPU-equipped drone carrying the pre-processed biological sample at the receiving destination;

removing the pre-processed biological sample from the SPU-equipped drone;

notifying a sender of the received pre-processed biological sample; and returning the SPU-equipped drone to the sending destination or sending the SPU-equipped drone to another destination.

3. The method of claim 1, further comprising maintaining the temperature of the biological sample within the SPU while the centrifuge is operating during the time of aerial transport.

4. The method of claim 1, wherein the biological sample comprises blood, tissue, plasma, serum, organ, urine, saliva, or other body fluid.

5. The method of claim 1, wherein the processing comprises generating a counter force to a force generated by the centrifuge.

6. A method for transporting and processing biological materials, comprising the steps of:

providing a sample processing unit (SPU)-equipped drone for transporting and processing biological materials, the SPU-equipped drone comprising: a drone having a drone body and propellers; and a sample processing unit (SPU) connected to the drone body, wherein the SPU comprises a centrifuge for processing a biological sample, the centrifuge including a mechanism to counter a force produced by a centrifuge action, the mechanism configured to generate a counterforce and comprising a motor-driven gear arrangement adapted to rotate two independent shafts in opposite directions, the mechanism configured to operate independently of the propellers;

collecting the biological sample;

placing the biological sample into the SPU-equipped drone;

activating the SPU of the SPU-equipped drone at a sending destination; and processing the biological sample by at least the centrifuge at the same time of aerial transport.

7. The method of claim 6, further comprising the steps of:

setting a receiving destination and deploying the SPU-equipped drone for aerial transport of the biological sample;

notifying the receiving destination of the incoming biological sample arriving by the SPU-equipped drone;

executing a flight path of the SPU-equipped drone while at the same time processing the biological sample;

receiving the SPU-equipped drone carrying the pre-processed biological sample at the receiving destination;

removing the pre-processed biological sample from the SPU-equipped drone;

notifying a sender of the received pre-processed biological sample; and returning the SPU-equipped drone to the sending destination or sending the SPU-equipped drone to another destination.

8. The method of claim 6, further comprising maintaining the temperature of the biological sample within the SPU while the centrifuge is operating during the time of aerial transport.

9. The method of claim 6, wherein the biological sample comprises blood, tissue, plasma, serum, organ, urine, saliva, or other body fluid.

10. The method of claim 6, wherein the processing comprises generating a counter force to a force generated by the centrifuge.

* * * * *